United States Patent [19]
Flynn et al.

[11] Patent Number: 5,354,757
[45] Date of Patent: Oct. 11, 1994

[54] AZANORADAMANTANES

[75] Inventors: Daniel L. Flynn, Mundelein; Alan E. Moormann, Skokie, both of Ill.

[73] Assignee: G. D. Searle & Co., Chicago, Ill.

[21] Appl. No.: 991,028

[22] Filed: Dec. 15, 1992

[51] Int. Cl.$^5$ .................. A61K 31/445; C07D 221/22
[52] U.S. Cl. ...................................... 514/290; 546/79
[58] Field of Search .................... 546/94, 79; 514/294, 514/290

[56] References Cited

U.S. PATENT DOCUMENTS

| | | | |
|---|---|---|---|
| 4,578,382 | 3/1986 | Jarreau et al. | 514/245 |
| 4,816,453 | 3/1989 | Watts | 514/217 |
| 4,950,759 | 8/1990 | Wijngaarden et al. | 546/94 |
| 4,992,461 | 2/1991 | Zabrowski et al. | 514/413 |
| 5,001,133 | 3/1991 | Richardson et al. | 514/304 |
| 5,126,343 | 6/1992 | Zabrowski et al. | 514/243 |
| 5,137,893 | 8/1992 | Becker et al. | 514/293 |
| 5,140,023 | 8/1992 | Becker et al. | 514/214 |

FOREIGN PATENT DOCUMENTS

| | | |
|---|---|---|
| 0189002 | 7/1986 | European Pat. Off. |
| 2152049A | 7/1985 | United Kingdom |
| 2193633A | 2/1988 | United Kingdom |
| 2231265A | 11/1990 | United Kingdom |

OTHER PUBLICATIONS

Sandoz AG New N-oxide(s) of alkylene bridged piperidinol etc. Derwent 89/179167/25 B0025,26 Jun. 1989.

R. C. Bick et al, Aristofruticosine, A Novel Indole Alkaloid etc. Tetrahedron Letters, V. 29, N. 27, 3355–3356 Jan. 1988.

Theo R. Bok et al., 3-Azanoradamantanes Heterocycles, V. 12, N. 3, 343–347, Jan 1979.

Rene Beerli et al., Synthesis of Aristotelia-Type of Alkaloids Helvetica Chimica Acta, V. 74, 110–116, Jan. 1991.

Primary Examiner—Marianne M. Cintins
Assistant Examiner—Phyllis G. Spivack
Attorney, Agent, or Firm—Cynthia S. Kovacevic; Roger A. Williams

[57] ABSTRACT

This invention relates to compounds of the formula:

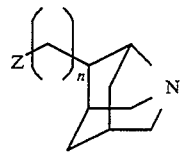

or a pharmaceutically acceptable salt thereof wherein Z is selected from the group consisting of

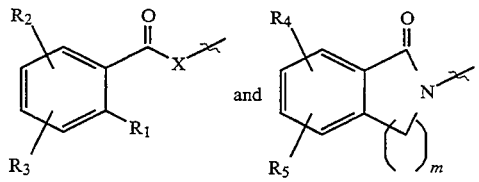

$R_1$ is alkoxy of one to six carbon atoms;

$R_2$, $R_3$, $R_4$ and $R_5$ are the same or different and are selected from the group consisting of hydrogen, halogen, $CF_3$, hydroxy, alkoxy of one to six carbon atoms, acyl of two to seven carbon atoms, amino, amino substituted by one or two alkyl groups of one to six carbon atoms, $C_2$-$C_7$ acylamino, aminocarbonyl, aminosulfone optionally substituted by one or two alkyl groups of one to six carbon atoms, $C_1$-$C_6$ alkylsulfone and nitro;

n is 0, 1 or 2;

m is 0 or 1;

X is O or $NR_7$; and $R_7$ is hydrogen or alkyl of 1 to 6 carbon atoms.

9 Claims, No Drawings

AZANORADAMANTANES

BACKGROUND OF THE INVENTION

The present invention relates to pharmaceutical agents (compounds) which act as 5-HT$_4$ agonists or antagonists and/or 5-HT$_3$ antagonists in mammals. As serotonin 5-HT$_4$ agonists, these compounds are gastrointestinal prokinetic agents useful for the treatment of human gastrointestinal (GI) hypomotility disorders such as reflux esophagitis, gastroparesis, nonulcer dyspepsia, ileus, constipation and irritable bowel syndrome (constipation predominant). As serotonin 5-HT$_4$ antagonists these compounds are useful in the treatment of motility disorders of the GI tract such as diarrhea and irritable bowel syndrome (diarrhea predominant). As serotonin 5-HT$_3$ antagonists these compounds are useful in slowing colonic transport and therefore are useful in the treatment of diarrhea predominant irritable bowel syndrome. The serotonin 5-HT$_4$ agonists or antagonists and/or serotonin 5-HT$_3$ antagonists are also useful in the treatment of emesis, anxiety, visceral pain, substance abuse (either cravings or withdrawal syndrome), cognitive disorders and other CNS disorders wherein treatment with a serotonin 5-HT$_4$ agonist or antagonist and-/or serotonin 5-HT$_3$ antagonist would be indicated.

Serotonin (5-hydroxytryptamine; 5-HT) functions as a neurotransmitter in the mammalian central nervous system (CNS) and in the periphery. Serotonin is unsurpassed among monoamine neurotransmitters in the number of receptor subtypes identified. To date, the number of subtypes is into the teens, including the major subtypes 5-HT1A, 1B, 1C, 1D, 1E, 2A, 2B, 3 (perhaps subtypes), 1P, serotonin transporter, etc. Because of the multiplicity of serotonin receptor subtypes, the identification of which serotonin receptor subtype is correlated to various physiological/pharmacological actions is complicated.

Serotonin has been known for some years to promote peristalsis in the GI tract in various animal models. During the mid 1980s, several specific antagonists to the 5-HT$_3$ receptor subtype were identified from independent laboratories. These 5-HT$_3$ antagonists were shown to be prokinetic in various rodent models. Hence, many publications and patents have issued wherein 5-HT$_3$ antagonists are claimed to be useful as GI prokinetic agents to treat various human hypomotility states: reflux esophagitis, nonulcer dyspepsia, gastroparesis, ileus, irritable bowel syndrome.

Gunning and Naylor (J. Pharm. Pharmacol. 1985, 37, 78) reported that metoclopramide (a 5-HT$_3$ antagonist which blocks the 5-HT3-mediated Bezold Jarisch reflex) enhanced electrical-field stimulated contractions in guinea pig stomach strips. Simultaneously, Buchheit et al (J. Pharm. Pharmacol. 1985, 37, 664) reported that three 5-HT$_3$ antagonists [metoclopramide, ICS-205930, and MDL 72222] both enhanced guinea pig stomach muscle strip contraction in vitro and led to increases in gastric emptying rates in vivo. H. Kimura et al (*Jpn. J. Pharmacol.*, 49 (suppl.) Mar. 25–28, 1989, 196pp) independently reported that SN-307, a selective 5-HT$_3$antagonist, enhanced transit of a charcoal meal in mice. J. S. Gidda et al (Gastroenterology 1988, 95, A867) reported that several 5-HT$_3$ antagonists [ICS-205930, GR38032, and zacopride] enhanced gastric emptying. From these reports it was concluded that serotonin 5-HT$_3$ antagonists would be useful agents for the therapeutic treatment of human GI dysmotilities where restoration of peristalsis and enhancement of transit is indicated.

More recently several clinical reports indicate that 5-HT$_3$ antagonists do not accelerate GI transit in man. Talley et al (Digestive Diseases and Sciences 1989, 34, 1511) has reported that GR38032, a selective 5-HT$_3$ antagonist, did not alter small intestinal transit times or mouth-to-cecum transit times. The conclusion was that GR38032 does not have a major effect on GI transit in man. Another clinical report by S. Gore et al (Aliment. Pharmacol. Therap. 1990, 4, 139) has demonstrated that GR38032 not only failed to accelerate GI transit, but in fact slowed colonic transit in man. Thus while 5-HT$_3$ antagonists do accelerate GI transit in rodent species (guinea pig, mouse, rat), they do not affect small bowel transit in man, and decrease, rather than increase, colonic transit.

Canine models of GI transit may more accurately reflect human results. J. M. Van Nueten et al (British J. Pharmacology, 1989, 96, 331P) reported recently that cisapride (a reported 5-HT$_3$ antagonist) enhanced antroduodenal motility in dogs, whereas ICS-205930, another potent 5-HT$_3$ antagonist did not. Moreover, ICS-205930 did not affect the responses to cisapride when the agents were coadministered. Nemeth and Gullikson (European J. Pharmacology, 1989, 166, 387) reported that the ability of BRL-24924 and cisapride to depolarize myenteric neurons was unrelated to their properties of 5-HT$_3$ antagonism.

The receptor mechanism by which cisapride, BRL-24924, metoclopramide, and other serotonergic agents are prokinetic is not related to their 5-HT$_3$ antagonist properties. The receptor mechanism responsible for their prokinetic activities is serotonergic, but at a serotonin receptor subtype, presently referred to as 5-HT$_4$. (M. Tonini et al Pharmacological Research, 1991, 24, 5).

Initially this clarification came from the laboratory of A. Dumuis, M. Sebben and J. Bockaert (Naunyn-Schmiedeberg's Arch. Pharmacol 1989, 340, 403). The prokinetic activity of a variety of benzamides, including cisapride and BRL-24924, were found to correlate with agonist activity at a novel 5-HT$_4$receptor subtype identified in mouse embryonic colliculi neurons. Shortly thereafter, D. Craig and D. Clarke identified the 5-HT$_4$ receptor in the myenteric plexus of the guinea pig ileum (J. Pharmacol. Exp. Ther., 1990, 252, 1378). Quite recently Craig and Clarke also demonstrated that the peristaltic reflex evoked by serotonin and the benzamide BRL-24924 (renzapride) was mediated through agonism at 5-HT$_4$receptors.

The natural product aristofruiticosine which contains an azanoradamantane nucleus is discussed in *Tetra Lett.*, 1988, 29, 3355 and *Helv. Chem. Acta.*, 1991, 74, 110.

An azanoradamantane nucleus substituted with nitriles or carboxyl groups is reported in *Hetrocycles*, 1979, 12, 343.

There is a need in the area of serotonin regulation for agents with broad clinical usefulness. Serotonin is one of the newer neurotransmitters to be recognized for physiological importance and agents which interact with 5-HT receptors are currently the focus of much research. P. Bonate, *Clinical Neuropharmacology*, Vol. 14, No. 1, pp. 1–16 (1991).

Accordingly, it is the object of this invention to produce compounds for use as pharmaceutical agents which will exhibit 5-HT$_4$ serotonin agonist or antagonist and/or 5-HT$_3$ serotonin antagonist activity in mammals. The compounds of the present invention meet the need for an agent which has broad clinical usefulness for treating conditions affected by 5-HT$_4$agonists or antagonists and/or 5-HT$_3$ antagonists in mammals by administering therapeutically effective amount of the compounds.

SUMMARY OF THE INVENTION

This invention relates to compounds of the formula I

or a pharmaceutically acceptable salt thereof wherein Z is selected from the group consisting of

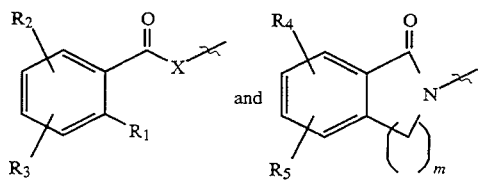

$R_1$ is alkoxy of one to six carbon atoms;

$R_2$, $R_3$, $R_4$ and $R_5$ are the same or different and are selected from the group consisting of hydrogen, halogen, $CF_3$, hydroxy, alkoxy of one to six carbon atoms, acyl of two to seven carbon atoms, amino, amino substituted by one or two alkyl groups of one to six carbon atoms, $C_2$–$C_7$ acylamino, aminocarbonyl, aminosulfone optionally substituted by one or two alkyl groups of one to six carbon atoms, $C_1$–$C_6$ alkylsulfone and nitro;

n is 0, 1 or 2;

m is 1 or 2;

X is O or $NR_7$; and $R_7$ is hydrogen or alkyl of one to six carbon atoms.

The present invention also provides pharmaceutical compositions comprised of a therapeutically effective amount of the compounds of Formula I in combination with a pharmaceutically acceptable carrier and a method for treating conditions responsive to 5-HT$_4$ serotonin agonist or antagonist and/or 5-HT$_3$ serotonin antagonist compositions.

DETAILED DESCRIPTION OF THE INVENTION

This invention encompasses compounds of the Formula I as previously described.

Within the class of compounds defined by Formula I, there is a sub-class of preferred compounds represented by Formula II:

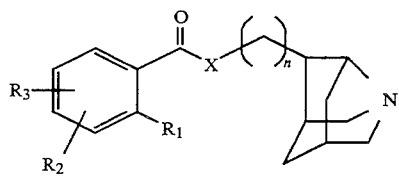

or a pharmaceutically acceptable salt thereof wherein
$R_1$ is alkoxy of one to six carbon atoms;
$R_2$, $R_3$, $R_4$ and $R_5$ are the same or different and are selected from the group consisting of hydrogen, halogen, $CF_3$, hydroxy, alkoxy of one to six carbon atoms, acyl of two to seven carbon atoms, amino, amino substituted by one or two alkyl groups of one to six carbon atoms, $C_2$–$C_7$ acylamino, aminocarbonyl, aminosulfone optionally substituted by one or two alkyl groups of one to six carbon atoms, $C_1$–$C_6$ alkylsulfone and nitro;
n is 0, 1 or 2;
X is NH.

Included within the preferred subclass of compounds of the Formula II are:
 4-amino-5-chloro-N-(hexahydro-2β,6β-methano-1H,7aα-pyrrolizin-1R, 1α-ylmethyl)-2-methoxybenzamide;
 4-amino-5-chloro-N-(hexahydro-2β,6β-methano-1H,7aα-pyrrolizin-1S,1α-ylmethyl)-2-methoxybenzamide;
 4-amino-5-chloro-N-(hexahydro-2β,6β-methano-1H,7aα-Pyrrolizin-1β-ylmethyl)-2-methoxybenzamide; and
 4-amino-5-chloro-N-(hexahydro-2β,6β-methano-1H,7aα-pyrrolizin-1α-ylmethyl)-2-methoxybenzamide.

Included within the classes and subclasses of compounds embraced by Formulas I-II are pharmaceutically acceptable salts of such compounds.

In the structures herein a bond drawn across a bond in a ring indicates that the bond can be to any available atom of the ring structure.

The term "pharmaceutically acceptable salt," as used herein, refers to conventionally accepted pharmaceutical salts prepared by processes which are well known to those of ordinary skill in the art. [See for example, S. M. Berge, et al., "Pharmaceutical Salts," *J. Pharm. Sci.*, 66:1–19 (1977)].

The term "composition" as used herein means a product which results from the mixing or combining of more than one element or ingredient.

The term "pharmaceutically acceptable carrier" as used herein means a pharmaceutically-acceptable material, composition or vehicle, such as a liquid or solid filler, diluent, excipient, solvent or encapsulating material, involved in carrying, formulating, or transporting a chemical agent.

The term "therapeutically effective amount" shall mean that amount of drug or pharmaceutical agent that will elicit the biological or medical response of a tissue, system or animal (mammal) that is being sought by a researcher or clinician.

The term "alkyl" as used herein means a univalent hydrocarbon radical having from one to twelve carbon atoms, more preferably from one to six carbon atoms and derived by the removal of a single hydrogen atom from a straight or branched chain saturated hydrocarbon. Representative of such radicals are methyl, ethyl, n-propyl, isopropyl, n-butyl, sec-butyl, isobutyl, tert-butyl, n-octyl, 2,4-dimethylpentyl and the like.

The term "alkoxy" as used herein means an alkyl radical, as defined above having one or more oxygen atoms attached thereto. Representative alkoxy groups include methoxy, ethoxy, propoxy, tert-butoxy and the like.

The term "halogen" as used herein means a fluoro, chloro, bromo or iodo radical.

The term "amino" as used herein is represented by the radical —NR₈R₉ wherein R₈ and R₉ are independently hydrogen or an alkyl group as previously described.

The term "acylamino" as used herein is represented by the radical

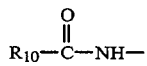

wherein R₁₀ is an alkyl group as described above.

The term "aminosulfone" as used herein is represented by the radical R₁₁—SO₂—NH— wherein R₁₁ is an alkyl group as defined above.

The term "aminocarbonyl" as used herein is represented by the radical

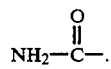

The compounds herein exhibit 5-HT₄ agonism or antagonism and/or 5-HT₃ antagonism. The 5-HT₃ activity possessed by the compounds of this invention was determined by the radioligand receptor binding assay as described herein. 5-HT₄ agonist activity was determined in the in vitro rat tunica muscularis mucosae (TMM) assay described herein. (Baxter et al., Naunyn Schmied Arch. Pharmacol, 1991, 343, 439). Similarly, use of the rat TMM assay may be employed to identify 5-HT₄ antagonists which block the action of serotonin. One with skill in the art could determine the activity of the compounds of the present invention using the methodology of these assays, described herein, without undue experimentation.

The compounds of the invention having X=NH and the phthalimidines exhibit 5-HT₄ agonist activity which is associated with the planar conformation of the molecules. The benzamide compounds are forced into a planar conformation via internal hydrogen bonding. The other compounds of the invention exhibit 5-HT₄ activity which on a continuum can be antagonist activity or a mixed or partial agonist/antagonist activity.

By virtue of their activity as 5-HT₄ agonists or antagonists and/or 5-HT₃ antagonists the compounds of Formula I and II are useful in treating conditions such as gastrointestinal motility disorders, emesis, anxiety, cognitive disorders and other CNS disorders. As used herein gastrointestinal motility disorders responsive to treatment with 5-HT₄ agonists include reflux esophagitis, non-ulcer dyspepsia, gastroparesis, ileus, irritable bowel syndrome (constipation predominant), constipation, and the like. As used herein gastrointestinal motility disorders responsive to treatment with 5-HT₄ antagonists include diarrhea, irritable bowel syndrome (diarrhea predominant) and the like. As used herein disorders responsive to 5-HT₃ antagonists include emesis due to either cancer chemotherapy or operative procedures, anxiety, cognitive disorders, drug abuse (either cravings or withdrawal syndrome), irritable bowel syndrome (diarrhea predominant) and the like. A physician or veterinarian of ordinary skill can readily determine whether a subject exhibits such a condition treatable with a 5-HT₄ agonist or antagonist or 5-HT₃ antagonist.

The compounds of the present invention can be administered in such oral dosage forms as tablets, capsules, softgels, pills, powders, granules, elixirs or syrups. The compounds can also be administered intravascularly, intraperitoneally, subcutaneously, intramuscularly or topically using forms known in the pharmaceutical art. In general the preferred form of administration is oral.

For the orally administered pharmaceutical compositions and methods of the present invention, the foregoing active ingredients will typically be administered in admixture with suitable pharmaceutical diluents, excipients or carriers (collectively referred to hereinafter as "carrier" materials). Such carrier materials are suitably selected with respect to the intended form of administration and consistent with conventional pharmaceutical practices.

For example, for oral administration in the form of tablets or capsules, a therapeutically effective amount of one or more compounds of the present invention can be combined with any oral pharmaceutically acceptable inert carrier such as lactose, starch, sucrose, cellulose, magnesium stearate, calcium sulfate and the like or various combinations thereof. For oral administration in liquid forms, such as in softgels, elixirs, syrups and the like, a therapeutically effective amount of the active drug components can be combined with any oral pharmaceutically acceptable inert carrier such as water, ethanol, polyethylene glycol, vegetable oils, propylene glycol, benzylalcohol and the like or various combinations thereof.

When desired or necessary, suitable binders, lubricants, disintegrating agents, preservatives, and coloring or flavoring agents can also be incorporated into the mixture. Suitable binders include starch, gelatin, natural sugars, corn sweeteners, natural and synthetic gums and waxes and the like, or combinations thereof. Lubricants can include boric acid, sodium benzoate, sodium acetate, sodium chloride and the like, or combinations thereof. Disintegrators include without limitation starch, methylcellulose, agar, bentonite, guar gum and the like, or combinations thereof.

For intravascular, intraperitoneal, subcutaneous or intramuscular administration, one or more compounds of the present invention can be combined with a suitable carrier such as water, saline, aqueous dextrose and the like. For topical administration therapeutically effective amounts of one or more compounds of the present invention can be combined with pharmaceutically acceptable creams, oils, waxes, gels and the like.

Regardless of the route of administration selected, a therapeutically effective amount of the compounds of the present invention are formulated into pharmaceutically acceptable dosage forms by conventional methods known to those skilled in the art. The dosages for preventing or treating conditions mediated by 5-HT₄ agonists or antagonists and/or 5-HT₃ antagonists with the compounds of the present invention is determined in accordance with a variety of factors, including the type, age, weight, sex and medical condition of patient, the severity of the condition, the route of administration and the particular compound employed in the treatment. A physician or veterinarian of ordinary skill can readily determine and prescribe the effective amount of drug required to prevent or arrest progress of the condition. In so proceeding, the physician or veterinarian could employ relatively low doses at first and subsequently increase the dose until a maximum response is obtained. The daily doses of the compounds of the invention are ordinarily in the range of about 1 to 1000 mg, more preferably in the range of about 10 to 500 mg.

The compounds of this invention are generally prepared according to the following reaction schemes I–V.
SCHEME I
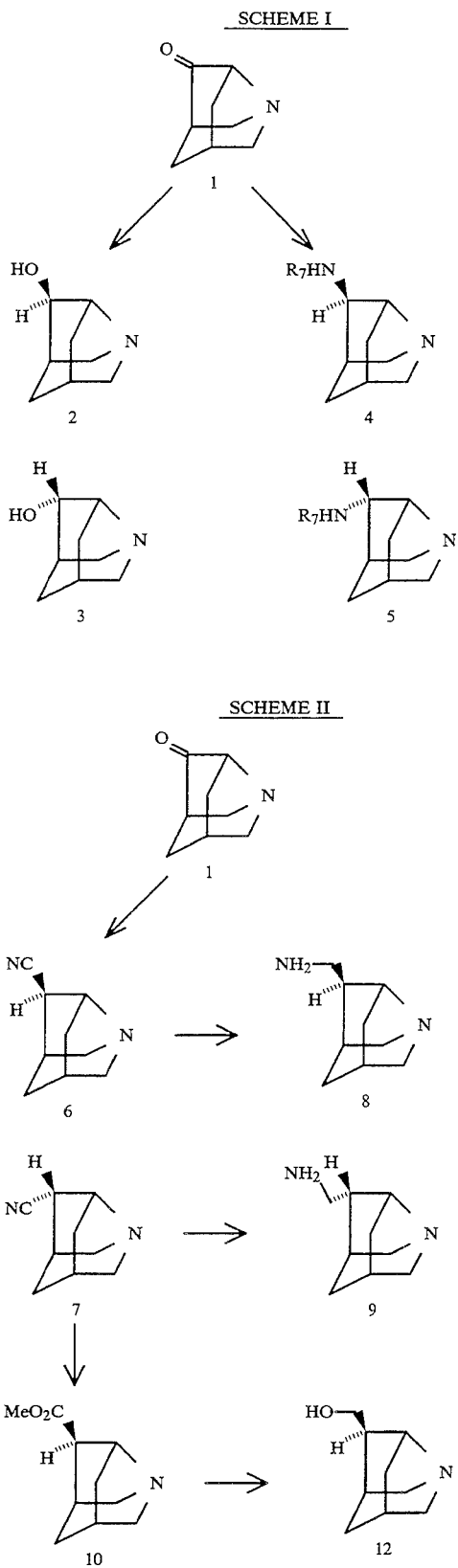
SCHEME II
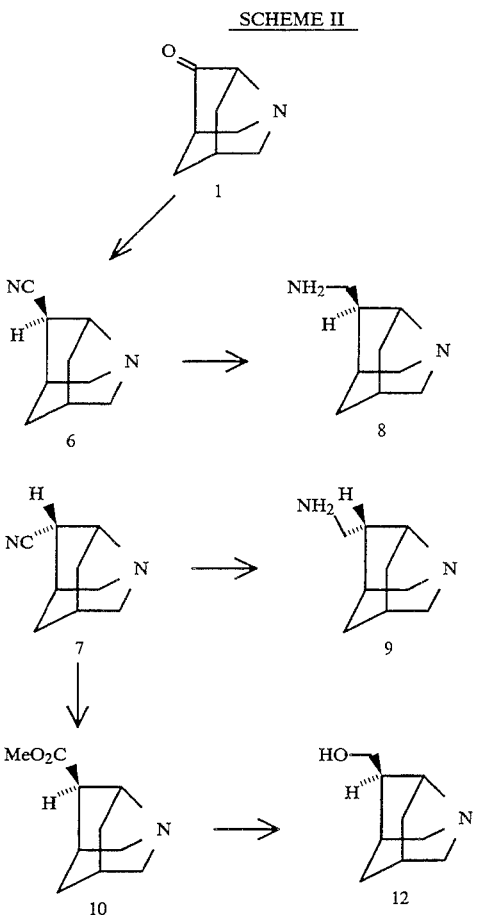
SCHEME II (continued)
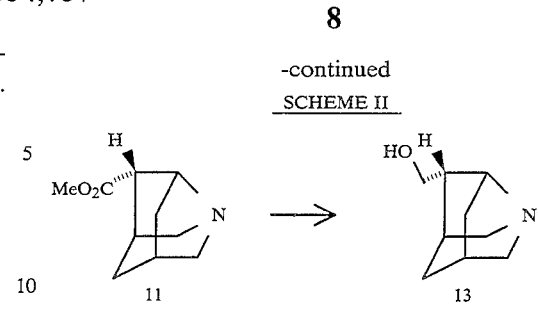
SCHEME III
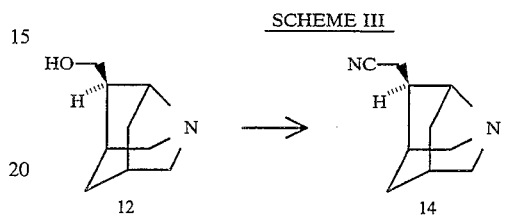
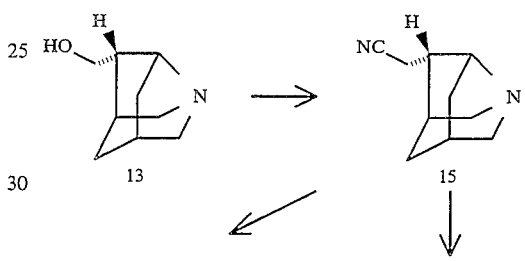
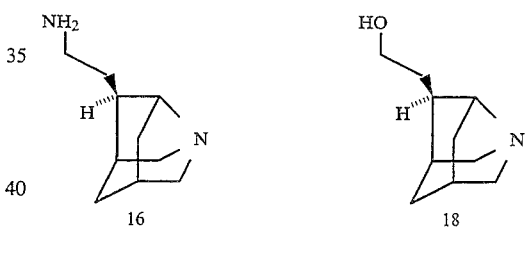
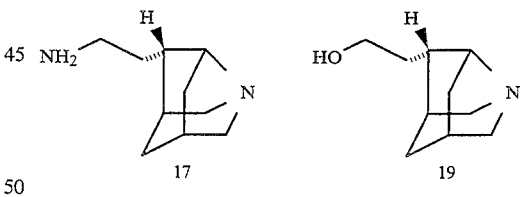
SCHEME IV
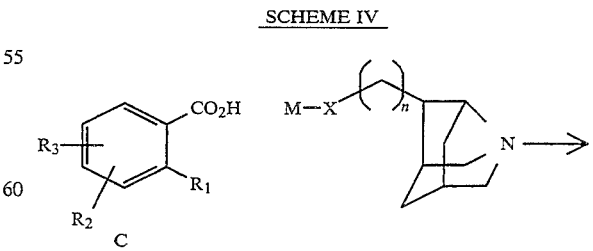
MX = HR$_7$N
(for compounds 4, 5, 8, 9, 16 or 17)
MX = HO or metallated alkoxide:
(for compounds 2, 3, 12, 13, 18, 19)

-continued
SCHEME IV

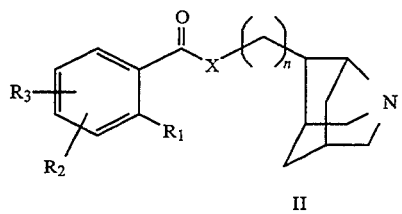

II

SCHEME V

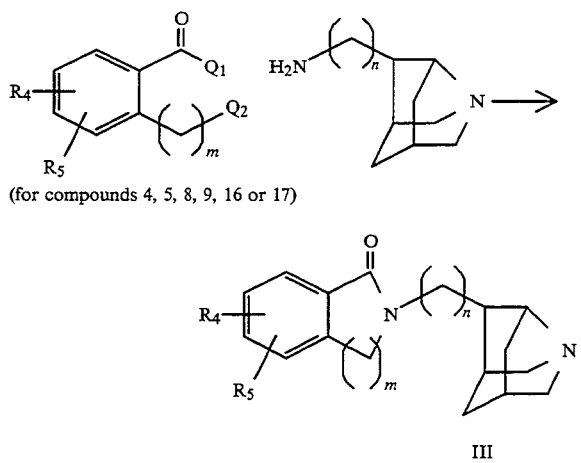

III

Chemical Preparation

The known 3-azanoradamantane-6-one 1 (T. R. Bok and W. N. Speckamp Heterocycles 1979, 12, 343) is utilized as shown in scheme I for the preparation of exo-3-azanoradamantane-6-ol 2 and endo-3-azanoradamantane-6-ol 3 by reducing 1 with sodium borohydride in methanol or with lithium aluminum hydride in tetrahydrofuran. Alternatively, reduction with sodium/alcohol mixtures affords a different ratio of the alcohols 2 and 3. The mixture of 2 and 3 is separated by silica gel chromatography.

The ketone 1 is also used to prepare the exo-3-azanoradamantane-6-amine 4 and the endo-3-azanoradamantane-6-amine 5 by conversion to its oxime derivative, followed by reduction with lithium aluminum hydride to give the primary amines ($R_7=H$). Alternatively, reaction of a primary amine with ketone 1 under conditions of reductive amination afford the secondary amines 4 and 5 wherein $R_7$ is alkyl.

In cases where n is I (see Formula II), the ketone 1 is reacted with tosylmethylisocyanide in the presence of base (preferably potassium t-butoxide) to afford the separable nitriles 6 and 7. See scheme II. These nitriles are individually reduced with lithium aluminum hydride in tetrahydrofuran to afford the exo-3-azanoradamantane-6-methylamine 8 and the endo-3-azanoradamantane-6-methylamine 9, respectively. Alternatively, the nitriles 6 and 7 are converted to their respective methyl esters 10 and 11 (methanol, HCl), which are then reduced with lithium aluminum hydride in an etheral solvent (preferably tetrahydrofuran) to give exo-3-azanoradamantane-6-methylcarbinol 12 and the endo-3-azanoradamantane-6-methylcarbinol 13, respectively.

Scheme III illustrates the preparation of substituted 3-azanoradamantanes wherein n is 2 (see Formula II). The methylcarbinols 12 and 13 are separately converted into intermediates wherein the alcohol functionality is a leaving group (e.g. tosylate). These tosylates are reacted with sodium cyanide in a polar aprotic solvent (dimethylformamide) to afford the exo- and endo-cyanomethyl substituted compounds 14 and 15, respectively. Treatment of 14 and 15 individually with lithium aluminum hydride in an etheral solvent gives rise to the desired exo-3-azanoradamantane-6-($\beta$-amino)ethane 16 and the endo-3-azanoradamantane-6-($\beta$-amino)ethane 17. Alternatively, conversion of the nitriles 14 and 15 into their respective methyl esters as described above, followed by reduction with lithium aluminum hydride in an etheral solvent affords exo-3-azanoradamantane-6-($\beta$-hydroxy)ethane 18 and the endo-3-azanoradamantane-6-($\beta$-hydroxy)ethane 19.

Scheme IV illustrates the coupling of the substituted benzoic acids C with the appropriate amine or alcohol to afford compounds of formulae II. Typical acid-activating reagents (acid chloride, DCC, ECDI, CDI, etc.) are suitable for this coupling. Preferably CDI (carbonyldiimidazole) is used as the acid-activating reagent, with the coupling reaction being performed in dimethylformamide or tetrahydrofuran or a similar polar aprotic solvent. For the couplings involving the alcohols 2, 3, 12, 13, 18, or 19, preferably the alcohol is converted to a metallated alkoxide by use of an inorganic base such as sodium, potassium or cesium carbonate or alternatively sodium or potassium hydride.

Scheme V illustrates the process used to afford compounds of formula III. In Scheme V, Q1 and Q2 are independently leaving groups (e.g. chloride) or taken together are oxygen, m is 1 or 2, and $R_4$ and $R_5$ are as described above. Compounds of formulae D are reacted with the amines 4, 5, 8, 9, 16, or 17 in an inert solvent such as toluene, tetrahydrofuran, or dimethylformamide optionally in the presence of base such as potassium carbonate or cesium carbonate to afford the desired compounds III.

EXAMPLE A

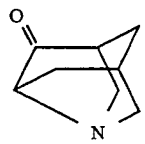

($\pm$) Hexahydro-2,6-methano-1H-pyrrolizin-1-one

The above compound was synthesized using the method of Theo Reints Bok and Nico Speckamp [*Heterocycles* Vol. 12 No. 3, pages 343–347 (1979).].

EXAMPLE B

Example B-1
2S-Hexahydro-2,6-methano-1H-pyrrolizin-1-one

Example B-2
2R-Hexahydro-2,6-methano-1H-pyrrolizin-1-one

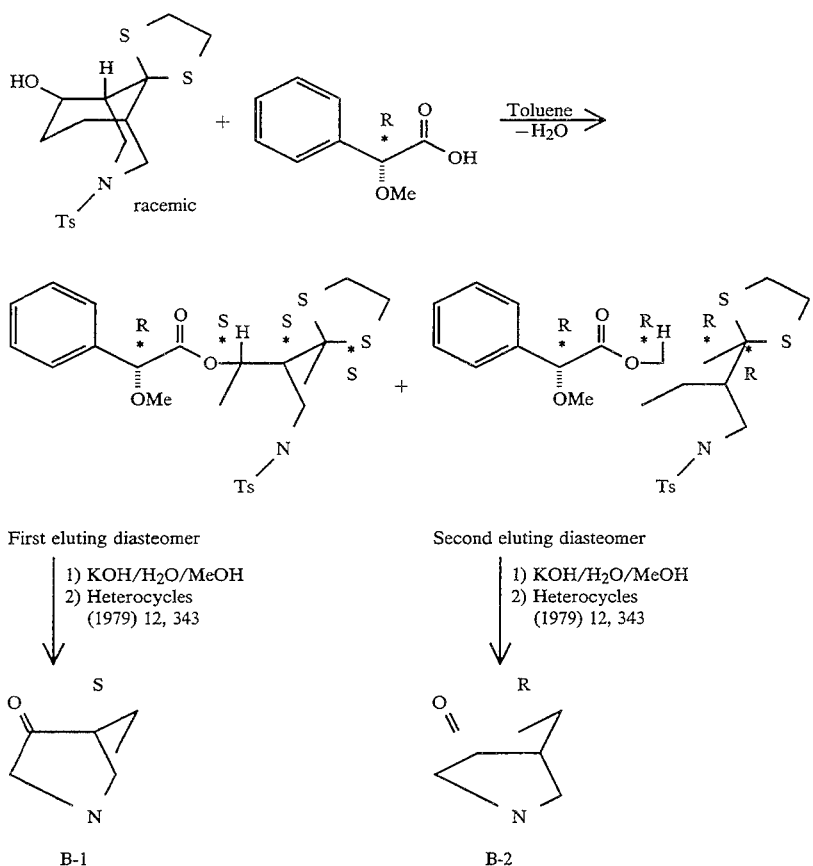

The racemic equatorial alcohol [N. Speckamp, et al. *Heterocycles* Vol. 12 No. 3, pages 343–347 (1979)] (30.0 g; 0.078 moles) and R-(—)-α-methoxyphenylacetic acid (13.8 g; 0.083 moles) were subjected to reflux with 100 mg of p-toluenesulfonic acid in 1.0 liter of toluene until tlc (40% EtOAc/toluene) indicated no further change. The reaction mixture was concentrated and the residue chromatographed on a Waters prep 500 using two cartridges and eluting with 5% EtOAc/CH$_2$Cl$_2$. The first compound to elute was collected in the first three 500 ml fractions. Concentration afforded 15.9 g.

HPLC Analysis:
Achiral column: Zorbax-RX-C-8; Mobile Phase 10/90 to 70/30 (30 min) MeCN/TEAP
Retention Time=13.46 min; 99.34% purity
Chiral Column: Chiralcel OD-R; Mobile Phase 60/40 MeCN/H$_2$O
Retention Time=49.40 min; 99+% purity The first component was dissolved in MeOH (500 ml) and 5.0 g of KOH in 20 ml of H$_2$O and the mixture was subjected to reflux for one hour. Tlc 40% EtOAc/toluene indicated the reaction was complete. The reaction mixture was concentrated and the residue was suspended in H$_2$O and filtered and washed with H$_2$O and suction dried to yield 7.9 g of a solid. Rotation (CHCl$_3$): α$_D$+3.0°. 200 mg of this solid was crystallized from MeOH. A crystal suitable for single crystal X-ray was obtained. The absolute configuration is shown below.

This alcohol was used to prepare the enantiopure 2S-hexahydro-2,6-methano-1H-pyrrolizin-1-one (Example B-1) utilizing the synthetic route of Speckamp (*Heterocycles* Vol. 12, No. 3 pages 343–347 (1979)).

The second component was subjected to chromatography a second time to remove the 5% of the less polar component. The purified material was processed as described above to afford 2R-hexahydro-2,6-methano-1H-pyrrolizin-1-one (Example B-2).

EXAMPLE C (±) Hexahydro-2β,6β-methano-1H,7aα-pyrrolizine-1α-carbonitrile (C-1) and (±) hexahydro-2β,6β-methano-1H,7aα-pyrrolizine-1β-carbonitrile (C-2).

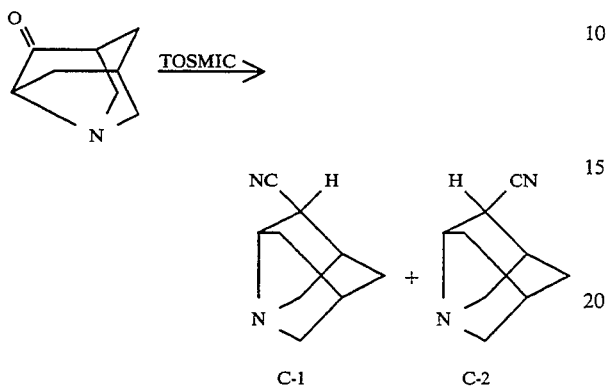

3-Azanoradamantan-6-one (320 mg; 0.00233 moles) tosylmethyl isocyanide (593 mg; 0.00303 moles) and 237 µl of ethanol were dissolved in 10 ml of ethylene glycol dimethyl ether (DME). This mixture was cooled to −68° C. in an acetone/dry ice bath. Potassium tert-butoxide (623 mg; 0.0055 moles) was added to the reaction mixture, and the reaction mixture was allowed to warm to room temperature. After two hours a solid formed which was filtered and washed with DME. The filtrate was concentrated to dryness. The residue was dissolved in 2.0 ml of water and the product extracted five times with 15 ml of Et$_2$O. The combined Et$_2$O layers were dried over MgSO$_4$ and concentrated to dryness. The resulting oil was purified by silica gel chromatography, eluting with 5% EtOH/CHCl$_3$ *0.5% NH$_4$OH. The nitrile (C-1) (124 mg) eluted first followed by the nitrile (C-2) (105 mg).

Example C-1: C$_9$H$_{12}$N$_2$ MW=148.20

NMR (CDCl$_3$) $^1$H (ppm): 1.62 (1H) doublet of triplets [J=13 Hz and J=2.5 Hz]; 1.82 (1H) doublet of doublet [J=13 Hz and J=5 Hz]; 1.9 to 2.05 (2H) multiplet; 2.22 (1H) singlet; 2.5 (1H) singlet; 2.87 (1H) doublet [J=13 Hz]; 2.42 (1H) singlet; 3.06 (1H) doublet of doublets [J=11 Hz and J=3 Hz]; 3.19 (1H) doublet of doublets [J=11 Hz and J=3 Hz]; 3.43 (1H) doublet of triplets [J=11 Hz and J=1 Hz]; 3.90 (1H) doublet [J=8].

CMR (CDCl$_3$) $^{13}$C (ppm); 33.65; 36.37; 41.40; 43.45; 44.38; 65.41; 65.61; 67.35; 121.42.

Example C-2: C$_9$H$_{12}$N$_2$ MW=148.20

NMR (CDCl$_3$) $^1$H (ppm): 1.8 to 2.0 (3H) multiplet; 2.25 (1H) singlet; 2.4 to 2.5 (2H) multiplet; 2.89 to 3.17 (5H) multiplet; 3.82 (1H) triplet [J=13 Hz];

CMR (CDCl$_3$) $^{13}$C (ppm) 30.37; 36.08; 38.46; 40.39; 40.67; 61.85; 66.25; 67.14; 123.42.

Similarly, the enantiomerically pure 3-azanoradamant-6-one isomers were reacted with tosylmethyl isocyanide to produce the enantiomerically pure nitriles.

Example C-3: Prepared from Example B-1

Hexahydro-2β,6β-methano-1H,7aα-pyrrolizine-1S,1α carbonitrile

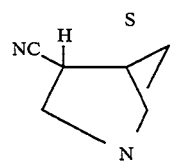

Example C-4: Prepared from Example B-2

Hexahydro-2β,6β-methano-1H,7aα-pyrrolizine-1R,1α-carbonitrile

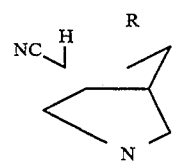

EXAMPLE D (±) Hexahydro-2β,6β-methano-1H,7aα-pyrrolizine-1α-methanamine

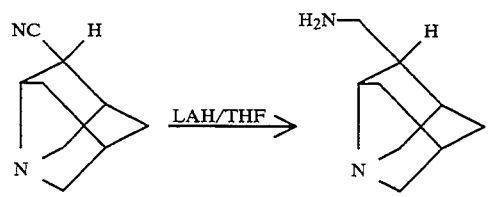

The nitrile of example C-1 (124 mg; 0.00083 moles) was added to a mixture of 1M LAH/THF (Lithium Aluminum, Hydride in Tetrahydrofuran) 1.0 ml and 1.0 ml of THF at room temperature. This mixture was heated to reflux for one hour. The reaction mixture was cooled and a solution of 100 µl water in 1.0 ml of THF was added to quench the excess LAH. This was followed by the addition of a solution of 100 µl 15% NaOH in 1.0 ml of THF. The resulting mixture was filtered and the solid washed with THF. The filtrate was concentrated to give 116 mg of the title compound as an oil.

C$_9$H$_{16}$N$_2$ MW=152.22

NMR (CDCl$_3$) $^1$H (ppm): 1.58 (1H) doublet of triplets [J=13 Hz and J=2.5 Hz]; 1.8 to 2.0 (2H) multiplet; 2.04 (1H) triplet [J=7.5 Hz]; 2.15 (1H) singlet; 2.21 (1H) singlet; 2.55 to 2.72 (3H) multiplet; 2.85 to 3.07 (3H); 3.14 (1H) doublet of triplets [J=11 Hz and J=1 Hz]; 3.49 doublet (1H) [J=6].

CMR (CDCl$_3$) $^{13}$C (ppm): 34.73; 36.34; 38.76; 43.11; 44.26; 58.11; 62.92; 64.15; 66.92.

Example D-1 (Prepared from Example C-3)

Hexahydro-2β,6β-methano-1H,7aα-pyrrolizine-1S,1α-methanamine

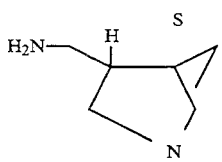

In an identical manner, the enantiomerically pure nitrile of Example C-3 was reacted to afford the title compound.

Example D-2 (Prepared from Example C-4)

Hexahydro-2β,6β-methano-1H,7aα-pyrrolizine-1R, 1α-methanamine

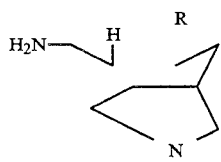

In an identical manner, the enantiomerically pure nitrile of Example C-4 was reacted to afford the title compound.

EXAMPLE E (±)Hexahydro-2β,6β-methano-1H,7aα-pyrrolizine-1β-methanamine

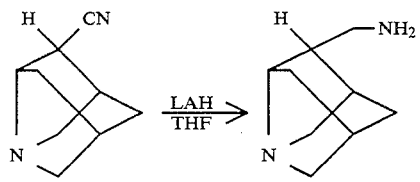

The nitrile of Example C-2 was reduced to the amine in the same manner as the nitrile in Example D.
$C_9H_{16}N_2$ MW=152.22

NMR (CDCl$_3$) $^1$H (ppm): 1.4 to 1.7 (4H) multiplet; 1.9 to 2.0 (2H) multiplet; 2.05 to 2.15 (2H) multiplet; 2.45 to 2.75 (1H) multiplet; 2.8 to 3.0 (4H) multiplet; 3.61 (1H) triplet [J=11 Hz];

CMR (CDCl$_3$) $^{13}$C (ppm): 28.44; 33.43; 35.95; 36.95; 41.13; 52.10; 62.34; 65.57; 66.04.

EXAMPLE 1

4-amino-5-chloro-N-(hexahydro-2β,6β-methano-1H,7aα-pyrrolizin-1α-ylmethyl)-2-methoxybenzamide

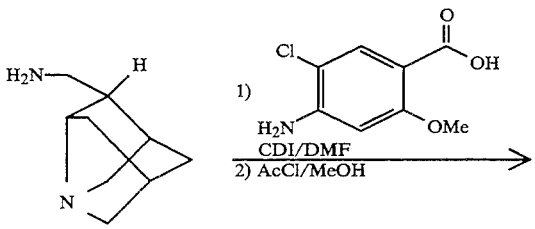

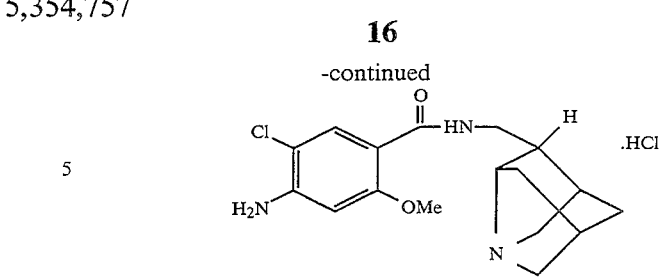

4-amino-5-chloro-2-methoxybenzoic acid (168 mg; 0.000836 moles) and 1,1'-carbonyldiimidazole (CDI) (154 mg; 0.00085 moles) were dissolved in 2.0 ml of dimethylformamide (DMF) and stirred for one hour. The amine of Example D (116 mg; 0.00082 moles) was dissolved in 2.0 ml of DMF and added to the above solution. This mixture was stirred for one hour and concentrated to dryness. The residue was dissolved in 1.0 ml of CHCl$_3$ and placed on a preparative thin layer chromatography plate and eluted with 30% MeOH/CHCl$_3$ 0.25 NH$_4$OH. The product was washed from the silica with MeOH saturated with NH$_3$ and the filtrate concentrated. The residue was dissolved in CHCl$_3$ and the solution filtered through celite. The filtrate was concentrated to yield 145 mg of the amide. The hydrochloride salt was prepared by dissolving the free base in a solution of HCl in MeOH prepared from acetyl chloride in MeOH, and concentrating the solution to dryness.

| $C_{17}H_{22}ClN_3O_2$ * 1.6 HCl * 1.5 H$_2$O MW = 421.19 | | |
|---|---|---|
| | Calc | Found |
| C | 48.48 | 48.55 |
| H | 6.37 | 6.02 |
| N | 9.98 | 9.91 |
| Cl | 21.88 | 22.09 |

EXAMPLE 2

4-amino-5-chloro-N-(hexahydro-2β,6β-methano-1H,7aα-pyrrolizin-1β-ylmethyl)-2-methoxybenzamide

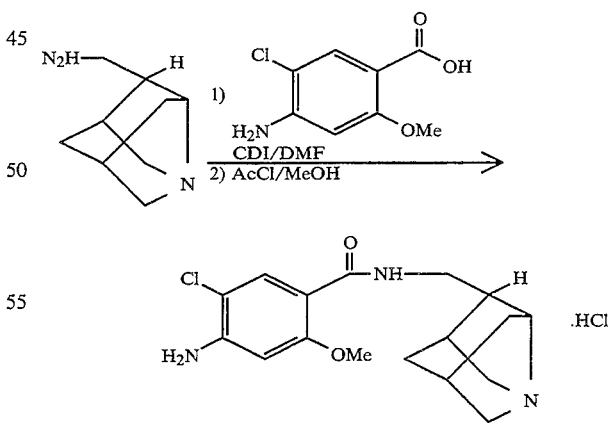

Following the procedure in Example 1 the title compound was synthesized using the amine of Example E.

| $C_{17}H_{22}Cl N_3O_2$ * 1.7 HCl * 2.0 H$_2$O * 0.2 MeOH MW = 440.26 | | |
|---|---|---|
| | Calc | Found |
| C | 46.92 | 47.21 |
| H | 6.52 | 6.14 |

| $C_{17}H_{22}Cl\ N_3O_2$ * 1.7 HCl * 2.0 $H_2O$ * 0.2 MeOH MW = 440.26 | | |
|---|---|---|
| | Calc | Found |
| N | 9.54 | 9.52 |
| Cl | 21.74 | 21.77 |

EXAMPLE 3

4-amino-5-chloro-N-(hexahydro-2β,6β-methano-1H,7aα-pyrrolizin-1S,1α-ylmethyl)-2-methoxybenzamide

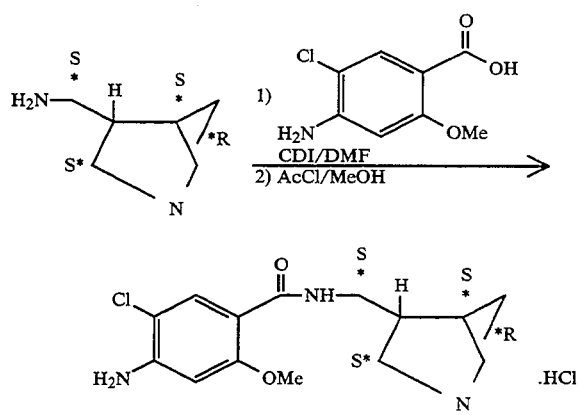

Following the procedure in Example 1 the title compound was synthesized using the amine prepared in Example D-1.

| $C_{17}H_{22}Cl\ N_3O_2$ * 1 HCl * 2.0 $H_2O$ MW = 408.32 | | |
|---|---|---|
| | Calc | Found |
| C | 50.01 | 50.11 |
| H | 6.66 | 7.04 |
| N | 10.29 | 10.05 |

Rotation (CHCl₃): $\alpha_D$ + 14.2° ± 0.718°.

EXAMPLE 4

4-amino-5-chloro-N-(hexahydro-2β,6β-methano-1H,7aα-pyrrolizin-1R,1α-ylmethyl)-2-methoxybenzamide

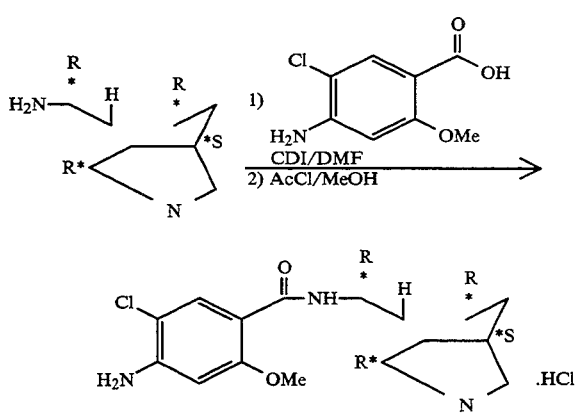

Following the procedure in Example 1 the title compound was synthesized using the amine prepared in Example D-2.

| $C_{17}H_{22}Cl\ N_3O_2$ * 1.6 HCl * 1.4 $H_2O$ MW = 372.29 | | |
|---|---|---|
| | Calc | Found |
| C | 48.69 | 48.39 |
| H | 6.34 | 6.16 |
| N | 10.03 | 10.43 |
| Cl | 22.98 | 22.02 |

A. In Vitro Functional Assay for Serotonin 5-HT₄ agonism: RAT TMM

Serotonin 5-HT₄ agonism was measured in the rat esophagus in vitro preparation as reported by Baxter et al (Naunyn. Schmied. Arch. Pharmacol. 1991, 343, 439). Agonist activity was determined utilizing relaxation of carbachol-contracted rat tunica muscularis mucosae. One 2 cm segment of intrathoracic esophagus proximal to the diaphragm was removed from male rats, weighing approximately 300 gm, and the outer muscle layers removed. The inner tunica muscularis mucosa was mounted under 0.2–0.3 g of tension in a tissue bath containing oxygenated Tyrode's solution at 37° C. Cortisterone acetate (30 μM) and fluoxetine (1 μM) were included in the buffer to prevent uptake of serotonin, as well as pargyline (10 μM) to inhibit monoamine oxidase. Following a 30 min equilibrium period, tissues were isometrically contracted with carbachol (3 μM) to obtain a tonic contraction. A stable plateau was obtained within 20 min when test compound was added cumulatively to relax the muscle strip. EC₅₀ values were obtained for each agonist in tissues from 5 rats. EC₅₀ values for agonists at this 5-HT₄ receptor are indicated in Table I.

TABLE I

| Entry | 5-HT₄ Agonism (Rat TMM) In Vitro Assay: EC50 values |
|---|---|
| Serotonin | 9 nM |
| Example 1 | 175 nM |
| Example 2 | 415 nM |
| Example 3 | 140 nM |
| Example 4 | 274 nM |
| Cisapride | 55 nM |

Additional Rat TMM assays (n=6) were performed for Examples 3 and 4 and the EC₅₀ results for Example 3 is 269 nM±66.7 nM and for Example 4 is 347.7 nM±87.3 nM.

b. Serotonin (5-HT3)

Procedure: GR65630 binds to the 5-HT₃ receptor. Brain Cortices were obtained from male rats and a membrane fraction prepared by standard techniques. 0.04 mg of membrane prep was incubated with 0.2 nM [³H]-GR65630 for 66 minutes at 22° C. Non-specific binding was estimated in the presence of 1 uM ICS 205-930. Membranes were filtered and washed 3 times and the filters were counted to determine [³H]-GR65630 specifically bound. (Kilpatrick G. J., Jones B. J. and Tyers M. B., Identification and Distribution of 5-HT₃ Receptors in Rat Brain Using Radioligand Binding Assay, Nature, 330, 746–748 (1987)).

Results: $K_d$=2.46 $B_{max}$=154 fmol/mg protein
% Specific Binding: 70

TABLE II

| Effect of Compounds on [H]-GR65630 Bound (0.2 nM) | |
|---|---|
| Compound | Ki |
| Cisapride | 1500 nM |

TABLE II-continued

| Effect of Compounds on [H]-GR65630 Bound (0.2 nM) | |
|---|---|
| Compound | Ki |
| Example 1 | 5.5 nM |
| Quipazine | 0.18 nM |
| ICS 205-930 | 0.51 nM |
| 5-HT | 0.39 uM |

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula:

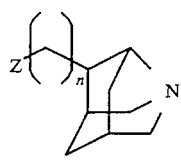

or a pharmaceutically acceptable salt thereof wherein Z is selected from the group consisting of

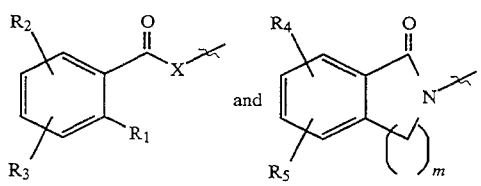

$R_1$ is alkoxy of one to six carbon atoms;
$R_2$, $R_3$, $R_4$ and $R_5$ are the same or different and are selected from the group consisting of hydrogen, halogen, $CF_3$, hydroxy, alkoxy of one to six carbon atoms, acyl of two to seven carbon atoms, amino, amino substituted by one or two alkyl groups of one to six carbon atoms, $C_2$–$C_7$ acylamino, aminocarbonyl, aminosulfone optionally substituted by one or two alkyl groups of one to six carbon atoms, $C_1$–$C_6$ alkylsulfone and nitro;
n is 0, 1 or 2;
m is 1 or 2
X is O or $NR_7$; and
$R_7$ is hydrogen or alkyl of 1 to 6 carbon atoms.

2. A compound as recited in claim 1 wherein Z is

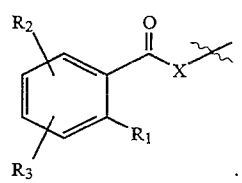

3. A compound as recited in claim 2 wherein X is NH.

4. A compound as recited in claim 3 which is 4-amino-5-chloro-N-(hexahydro-2β,6β-methano-1H,7aα-pyrrolizin-1R, 1α-ylmethyl)-2-methoxybenzamide of the formula

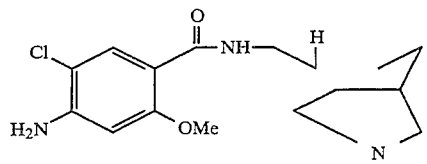

5. A compound as recited in claim 3 which is 4-amino-5-chloro-N-(hexahydro-2β,6β-methano-1H,7aα-pyrrolizin-1S,1α-ylmethyl)-2-methoxybenzamide of the formula

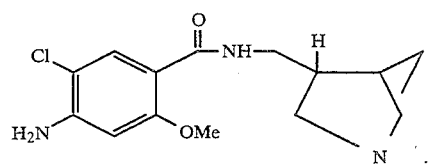

6. A compound as recited in claim 3 which is 4-amino-5-chloro-N-(hexahydro-2β,6β-methano-1H,7aα-pyrrolizin-1α-ylmethyl)-2-methoxybenzamide of the formula

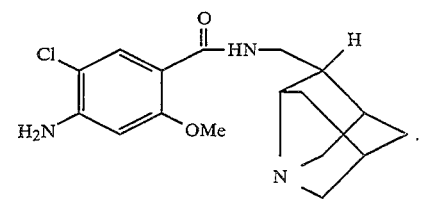

7. A compound as recited in claim 3 which is 4-amino-5-chloro-N-(hexahydro-2β,6β-methano-1H,7aα-pyrrolizin-1β-ylmethyl)-2-methoxybenzamide of the formula

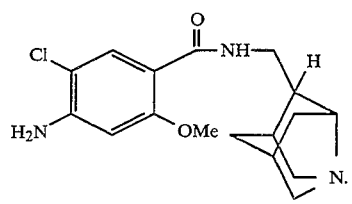

8. A pharmaceutical composition comprising a therapeutically effective amount of a compound of the formula:

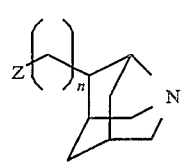

or a pharmaceutically acceptable salt thereof wherein Z is selected from the group consisting of

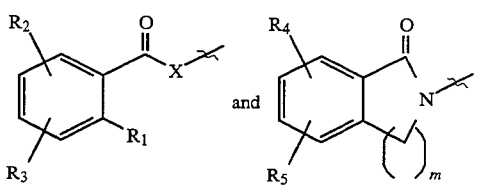

$R_1$ is alkoxy of one to six carbon atoms;

$R_2$, $R_3$, $R_4$ and $R_5$ are the same or different and are selected from the group consisting of hydrogen, halogen, $CF_3$, hydroxy, alkoxy of one to six carbon atoms, acyl of two to seven carbon atoms, amino, amino substituted by one or two alkyl groups of one to six carbon atoms, $C_2$–$C_7$ acylamino, aminocarbonyl, aminosulfone optionally substituted by one or two alkyl groups of one to six carbon atoms, $C_1$–$C_6$ alkylsulfone and nitro;

n is 0, 1 or 2;

m is 1 or 2;

X is O or $NR_7$;

$R_7$ is hydrogen or alkyl of 1 to 6 carbon atoms; and a pharmaceutically acceptable carrier.

9. A pharmaceutical composition as recited in claim 8 wherein the compound is selected from the group consisting of:

4-amino-5-chloro-N-(hexahydro-2β,6β-methano-1H,7aα-pyrrolizin-1R, 1α-ylmethyl)-2-methoxybenzamide;

4-amino-5-chloro-N-(hexahydro-2β,6β-methano-1H,7aα-pyrrolizin-1S,1α-ylmethyl)-2-methoxybenzamide;

4-amino-5-chloro-N-(hexahydro-2β,6β-methano-1H,7aα-pyrrolizin-1α-ylmethyl)-2-methoxybenzamide; and 4-amino-5-chloro-N-(hexahydro-2β,6β-methano-1H,7aα-pyrrolizin-1β-ylmethyl)-2-methoxybenzamide.

* * * * *

UNITED STATES PATENT AND TRADEMARK OFFICE
CERTIFICATE OF CORRECTION

PATENT NO. : 5,354,757  Page 1 of 4
DATED : October 11, 1994
INVENTOR(S) : Flynn, et al.

It is certified that error appears in the above-indentified patent and that said Letters Patent is hereby corrected as shown below:

Column 9, line 55, reading "n is I" should read -- n is 1 --.

Column 11, line 10, the formula reading

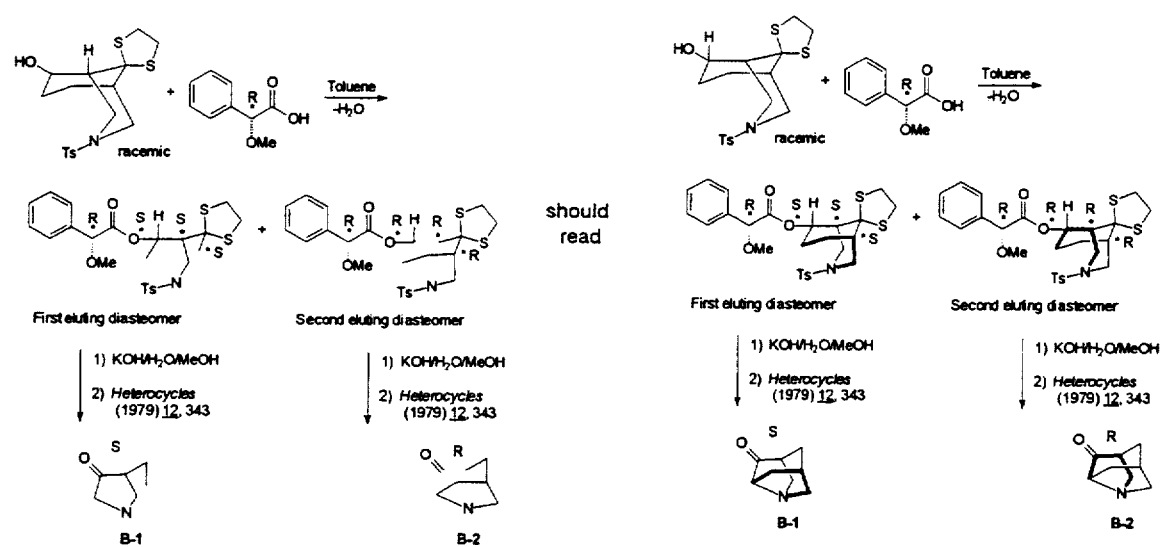

UNITED STATES PATENT AND TRADEMARK OFFICE
CERTIFICATE OF CORRECTION

PATENT NO. : 5,354,757  Page 2 of 4
DATED : October 11, 1994
INVENTOR(S) : Flynn, et al.

It is certified that error appears in the above-indentified patent and that said Letters Patent is hereby corrected as shown below:

Column 12, line 50, the formula reading

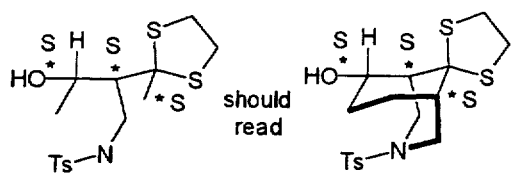

Column 14, line 5, the formula reading

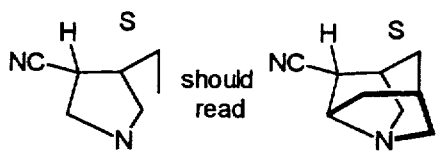

Column 14, line 15, the formula reading

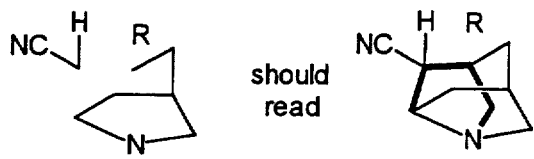

Column 15, line 2, the formula reading

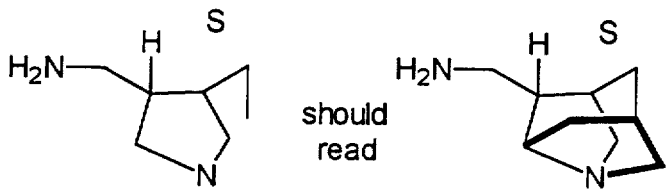

UNITED STATES PATENT AND TRADEMARK OFFICE
CERTIFICATE OF CORRECTION

PATENT NO. : 5,354,757                    Page 3 of 4
DATED      : October 11, 1994
INVENTOR(S): Flynn, et al.

It is certified that error appears in the above-indentified patent and that said Letters Patent is hereby corrected as shown below:

Column 15, line 20, the formula reading

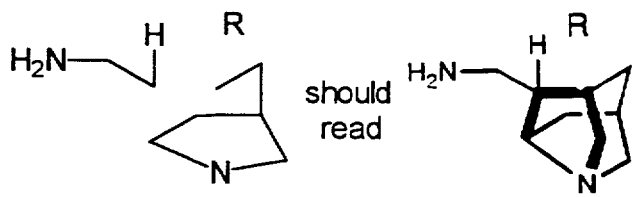

At column 17, lines 15 and 25, that part of the formula in both occurrences reading

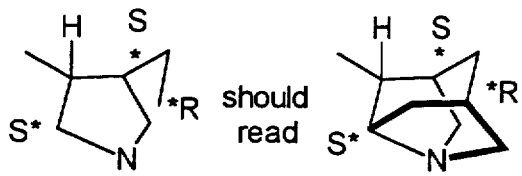

At column 17, lines 50 and 60, that part of the formula in both occurrences reading

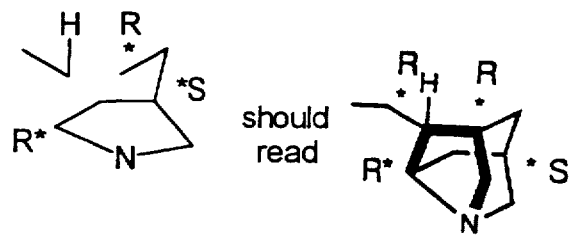

UNITED STATES PATENT AND TRADEMARK OFFICE
CERTIFICATE OF CORRECTION

PATENT NO. : 5,354,757

DATED : October 11, 1994

INVENTOR(S) : Flynn, et al.

It is certified that error appears in the above-indentified patent and that said Letters Patent is hereby corrected as shown below:

Column 20, line 3, that part of the formula reading

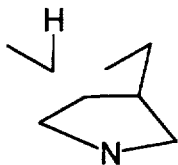 should read 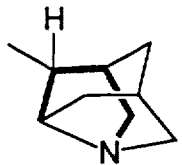

Column 20, line 17, that part of the formula reading

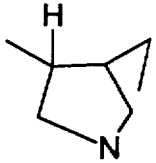 should read 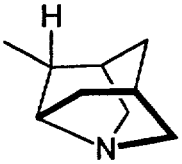

Signed and Sealed this

Twenty-sixth Day of September, 1995

Attest:

BRUCE LEHMAN

Attesting Officer

Commissioner of Patents and Trademarks